(12) United States Patent
Yoshida et al.

(10) Patent No.: US 11,376,328 B2
(45) Date of Patent: Jul. 5, 2022

(54) PHARMACEUTICAL COMPOSITION

(71) Applicant: Astellas Pharma Inc., Tokyo (JP)

(72) Inventors: Takatsune Yoshida, Tokyo (JP); Hiroyuki Kojima, Tokyo (JP); Yoshiaki Umemoto, Tokyo (JP); Sachie Namiki, Toyko (JP); Akira Takagi, Tokyo (JP); Ken Shimada, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 16/609,029

(22) PCT Filed: Apr. 27, 2018

(86) PCT No.: PCT/JP2018/017158
§ 371 (c)(1),
(2) Date: Oct. 28, 2019

(87) PCT Pub. No.: WO2018/199281
PCT Pub. Date: Nov. 1, 2018

(65) Prior Publication Data
US 2020/0138957 A1    May 7, 2020

(30) Foreign Application Priority Data
Apr. 28, 2017 (JP) .............................. JP2017-090299

(51) Int. Cl.
*A61K 47/32* (2006.01)
*A61K 31/4245* (2006.01)
*A61K 31/439* (2006.01)
*A61K 31/4422* (2006.01)

(52) U.S. Cl.
CPC .......... *A61K 47/32* (2013.01); *A61K 31/4245* (2013.01); *A61K 31/439* (2013.01); *A61K 31/4422* (2013.01)

(58) Field of Classification Search
CPC ..................................................... A61K 47/32
USPC ......................................................... 514/356
See application file for complete search history.

(56) References Cited

U.S. PATENT DOCUMENTS

2011/0152212 A1    6/2011   Crowther et al.

FOREIGN PATENT DOCUMENTS

| EP | 1739149 A1 | 1/2007 |
|---|---|---|
| JP | H09104620 A | 4/1997 |
| JP | 2010-519283 A | 6/2010 |
| JP | 2013087074 A | 5/2013 |

OTHER PUBLICATIONS

Pourbaghi-Masouleh et al., Nanoscale Res. Lets. (2013), 8:449, pp. 1-6.*
Dec. 8, 2020—(EP) Extended European Search Report—App. No. 18791303.3.
Suzuki H et al: "Influence of Water-Soluble Polymers on the Dissolution of Nifedipine Solid Dispersions With Combined Carriers", Chemical and Pharmaceutical Bulletin, Pharmaceutical Society of Japan, JP, vol. 46, No. 3, Mar. 1, 1998 (Mar. 1, 1998), pp. 482-487, XP000748996, ISSN: 0009-02363.
Brough et al., "Use of Polyvinyl Alcohol as a Solubility-Enhancing Polymer for Poorly Water Soluble Drug Delivery (Part 1)," AAPS PharmSciTech 17, 167-79, 2015.
Brough et al., "Use of Polyvinyl Alcohol as a Solubility-Enhancing Polymer for Poorly Water Soluble Drug Delivery (Part 2)," AAPS PharmSciTech 17, 180-90, 2015.
De Jaeghere et al., "Hot-melt extrusion of polyvinyl alcohol for oral immediate release," Int. J. Pharmaceutics 492, 1-9, 2015.
Ikeuchi-Takahashi et al., "Formulation and Evaluation of Morin-Loaded Solid Lipid Nanoparticles," Biol. Pharm. Bull. 39, 1514-22, 2016.
Oh et al., "A Mucoadhesive Polymer Prepared by Template Polymerization of Acrylic Acid in the Presence of Poly(vinyl Alcohol) for Mucosal Drug Delivery," J. Applied Polymer Science 94, 327-31, 2004.
Jul. 24, 2018—(PCT/JP) International Search Report—App 2018/017158.
U.S. Pharmacopeia National Formulary, USP 39, NF 34, vol. 3, 5448 Polymyxin / Official Monographs, 2016.
Japanese Pharmaceutical Excipients, 2013.
May 17, 2022—(JP) Office Action—App. No. 2019-514650.

* cited by examiner

*Primary Examiner* — Taofiq A Solola
(74) *Attorney, Agent, or Firm* — Banner & Witcoff, Ltd.

(57) ABSTRACT

Provided is a pharmaceutical composition in which the solubility and/or dissolution properties of a poorly-soluble drug can be improved. The pharmaceutical composition comprises a poorly-soluble drug, and polyvinyl alcohol having a saponification degree of 63 mol % or more and 67 mol % or less.

3 Claims, 6 Drawing Sheets

Figure 1
Intensity (cps)

Figure 2
Intensity (cps)

Figure 3
Intensity (cps)

Figure 4
Intensity (cps)

Figure 5
Intensity (cps)

PHARMACEUTICAL COMPOSITION

TECHNICAL FIELD

The present invention relates to a pharmaceutical composition, in which the solubility of a poorly-soluble drug is improved.

More particularly, the present invention relates to a pharmaceutical composition comprising a poorly-soluble drug and polyvinyl alcohol having a saponification degree of 63 mol % or more and 67 mol % or less.

BACKGROUND ART

In recent drug discovery research, poorly water-soluble drugs often become candidates for development. Alternatively, there is also a need to improve medical opportunities through early provision of therapeutic drugs in clinical settings, and general-purpose solubilization technology remains an important issue.

As methods of solubilizing a poorly-soluble drug, a method of amorphizing a poorly-soluble drug, and a method of preparing a solid dispersion of a poorly-soluble drug with a carrier, are known. Further, compositions, in which the solubility of a drug is improved by using polyvinyl alcohol as a carrier of a solid dispersion, are known (Non-patent literatures 1 and 2), but they do not necessarily show a sufficient effect on increasing the solubility of a drug.

CITATION LIST

Non-Patent Literature

[Non-patent literature 1] W. De Jaeghere et al, International Journal of Pharmaceutics, 492 (2015) 1-9, "Hot-melt extrusion of polyvinyl alcohol for oral immediate release applications"

[Non-patent literature 2] Chris Brough et al, AAPS PharmSciTech, Vol. 17, No. 1, February 2016, "Use of Polyvinyl Alcohol as a Solubility-Enhancing Polymer for Poorly Water Soluble Drug Delivery (Part 1)"

SUMMARY OF INVENTION

Technical Problem

Even in the current situation, formulation design to improve the solubility of poorly-soluble drugs is an important technical problem for the pharmacological effect expression of these drugs, and there is room for further improvement.

An object of the present invention is to provide a pharmaceutical composition in which the solubility of a poorly-soluble drug is improved.

Solution to Problem

By preparing a solid dispersion using a poorly-soluble drug and polyvinyl alcohol having a saponification degree of 63 mol % or more and 67 mol % or less, a high solubility was observed.

The present invention relates to:

[1] a pharmaceutical composition comprising a poorly-soluble drug, and polyvinyl alcohol having a saponification degree of 63 mol % or more and 67 mol % or less,

[2] the pharmaceutical composition according to claim 1, wherein the poorly-soluble drug has a solubility of 10 μg/mL or less in water,

[3] the pharmaceutical composition of [1] or [2], comprising a solid dispersion comprising the poorly-soluble drug and the polyvinyl alcohol,

[4] the pharmaceutical composition of any one of [1] to [3], wherein the poorly-soluble drug is amorphous, and

[5] use of polyvinyl alcohol having a saponification degree of 63 mol % or more and 67 mol % or less in the manufacture of a pharmaceutical composition comprising a poorly-soluble drug and having an improved solubility.

Advantageous Effects of Invention

According to the present invention, a pharmaceutical composition in which the solubility of a poorly-soluble drug is improved can be provided.

DESCRIPTION OF EMBODIMENTS

The term "to improve solubility" as used herein means that the solubility, the dissolved concentration, or the dissolution rate of a poorly-soluble drug in a solvent is increased. More particularly, as an embodiment, when a pharmaceutical composition comprising a poorly-soluble drug is evaluated by a dissolution test of Experimental Example 1, Experimental Example 2, or Experimental Example 3 described below, it is defined that the dissolved concentration of the poorly-soluble drug dissolved from the pharmaceutical composition during a predetermined period of time is higher than the solubility of the crystalline drug substance in water. With respect to methods for measuring the solubility, the dissolved concentration, and the dissolution rate of a poorly-soluble drug in a solvent, appropriate test methods for each drug may be used.

The term "solid dispersion" as used herein means a dispersion comprising a poorly-soluble drug and polyvinyl alcohol having a saponification degree of 63 mol % or more and 67 mol % or less, wherein most of the poorly-soluble drug exists in an amorphous form. The term "amorphous" as used herein means, in addition to the amorphous form, their transition states. The amorphous poorly-soluble drug exists as a solid solution that is homogeneously dispersed throughout polyvinyl alcohol having a saponification degree of 63 mol % or more and 67 mol % or less. The term "most" as used herein means that the crystal of the poorly-soluble drug accounts for 40% or less, preferably 20% or less, when the dispersion is prepared. As another embodiment, it means that the amount of the poorly-soluble drug crystal is 40% or less, preferably 20% or less, and more preferably 10% or less, when measured by powder X-ray diffraction, differential scanning calorimetry (DSC), or any other standard quantitative means. When it is measured by powder X-ray diffraction, a measurement using a θ/θ rotating anode XRD diffractometer is preferable.

The term "saponification degree" of polyvinyl alcohol as used herein means a saponification value determined by a measurement method described in The Japanese Pharmacopoeia, Seventeenth Edition, or a measurement method correlated with the measurement method, and can be calculated by the following equation (1). In connection with this, it is desirable that the measurement method has a correlation coefficient of 0.5 or more, and 0.6 or more in an embodiment, with the measurement method described in The Japanese Pharmacopoeia, Seventeenth Edition.

[Chem. 1]

(1)

Saponification degree (mol %) = m/(m + n) × 100
[m: number of hydroxyl groups, n: number of acetyl groups]

The term "polymerization degree" as used herein means an "average polymerization degree", and is defined as a value calculated on the basis of a viscosity value when evaluated according to the Japanese Pharmaceutical Excipients or a molecular weight measured by gel filtration or the like, or a value measured according to a measurement method correlated with the measurement method. Alternatively, it is defined as a value measured by (4) Measurement Method of Average Polymerization Degree in JIS K6726 "Testing methods for polyvinyl alcohol", or a value measured according to a measurement method correlated with the measurement method. In connection with this, it is desirable that the measurement method correlated with the measurement method of a viscosity value when evaluated according to the Japanese Pharmaceutical Excipients or gel filtration or the like is a measurement method having a correlation coefficient of 0.5 or more, and 0.6 or more in an embodiment, with the measurement method of a viscosity value when evaluated according to the Japanese Pharmaceutical Excipients or gel filtration or the like. Further, it is desirable that the measurement method correlated with (4) Measurement Method of Average Polymerization Degree in JIS K6726 "Testing methods for polyvinyl alcohol" is a measurement method having a correlation coefficient of 0.5 or more, and 0.6 or more in an embodiment, with (4) Measurement Method of Average Polymerization Degree in JIS K6726 "Testing methods for polyvinyl alcohol".

The term "poorly-soluble drug" as used herein means a drug having a low solubility in water. It should not be interpreted limitedly, so long as it is an active ingredient with a therapeutic effect or an active ingredient with a prophylactic effect. Examples of the poorly-soluble drug include a drug having a drug solubility in water of 10 μg/mL or less, preferably 0.01 μg/mL to 10 μg/mL, more preferably 0.1 μg/mL to 10 μg/mL, and still more preferably 1 μg/mL to 10 μg/mL.

The drug solubility in water of a drug may be determined, for example, in accordance with the method described in the General Notices of The Japanese Pharmacopoeia, Seventeenth Edition. More particularly, for example, it can be calculated as follows: After a drug is powdered and put into water, it is vigorously shaken at a temperature of 20±5° C. for 30 seconds each time at 5-minute intervals, and the drug solubility in water can be calculated from an amount dissolved within 30 minutes.

The poorly-soluble drug may be used in any form of a free form, a hydrate, or a pharmaceutically acceptable salt. The poorly-soluble drug may be used alone, or as a combination of two or more.

As polyvinyl alcohol used in the present invention, the saponification degree is 63 mol % or more and 67 mol % or less.

The polymerization degree of polyvinyl alcohol used in the present invention is not particularly limited, so long as it is pharmaceutically acceptable. More particularly, the polymerization degree is, for example, 50 or more and less than 1000, 50 or more and less than 600 in an embodiment, 100 or more and less than 500 in an embodiment, 100 or more and less than 300 in an embodiment, and 200 or more and less than 280 in an embodiment. Each lower limit and each upper limit above can be arbitrarily combined as desired.

In connection with this, polyvinyl alcohol has a function to improve the solubility of a poorly-soluble drug. The solubility of a poorly-soluble drug can be improved in a pH-independent manner by using polyvinyl alcohol in the present invention.

Examples of polyvinyl alcohol having a saponification degree of 63 mol % or more and 67 mol % or less include POVAL (registered trademark) JMR-10M (JAPAN VAM & POVAL CO., LTD., polymerization degree: 200 to 280, saponification degree: 63.0 to 67.0 mol %), and the like.

The content ratio of polyvinyl alcohol is not particularly limited, so long as the solubility of a poorly-soluble drug is improved. The content ratio of polyvinyl alcohol is, for example, 50% by weight to 700% by weight in an embodiment, and 100% by weight to 500% by weight in an embodiment, with respect to the weight of the poorly-soluble drug.

The pharmaceutical composition of the present invention may be a solid dispersion comprising a poorly-soluble drug and polyvinyl alcohol having a saponification degree of 63 mol % or more and 67 mol % or less.

The poorly-soluble drug contained in the pharmaceutical composition of the present invention may be in an amorphous state.

Examples of the pharmaceutical composition of the present invention include a solid preparation, such as tablets, capsules, granules, powder, or the like; and a liquid preparation, such as elixirs, suspensions, emulsions, or the like.

In the pharmaceutical composition of the present invention, it may be formulated by appropriately using various pharmaceutical additives, if desired, to the extent that the desired effects of the present invention can be achieved.

These pharmaceutical additives may be appropriately added alone, or as a combination of two or more, in appropriate amounts. With respect to the content ratios of the pharmaceutical additives, each pharmaceutical additive may be contained in an amount such that the desired effects of the present invention may be achieved.

The pharmaceutical composition of the present invention can be produced in accordance with methods including, for example, amorphization of a poorly-soluble drug, and the like.

The process of manufacturing the pharmaceutical composition of the present invention will be explained below.

Amorphization Step

The method of preparing a solid dispersion of a poorly-soluble drug and polyvinyl alcohol having a saponification degree of 63 mol % or more and 67 mol % or less is not particularly limited, so long as it is a conventional method of preparing a solid dispersion. Examples of the method include a solvent method, a hot melt extrusion method, a pulverization method, and the like.

(I) Solvent Method

Examples of the solvent method include a method in which after a poorly-soluble drug and polyvinyl alcohol having a saponification degree of 63 mol % or more and 67 mol % or less are dissolved and/or suspended in a solvent, the solvent is removed; and the like.

The solvent used is not particularly limited, so long as the poorly-soluble drug and polyvinyl alcohol having a saponification degree of 63 mol % or more and 67 mol % or less can be dissolved and/or suspended in the solvent. More particularly, examples of the solvent include methanol, dichloromethane, water, ethanol, acetone, propylene glycol, dimethyl sulfoxide, and the like; and the examples include methanol and water in an embodiment. These solvents can be appropriately used alone, or as a combination of two or more, in appropriate amounts.

Examples of a method of removing the solvent include spray drying, evaporation, freeze drying, and the like; and the examples include spray drying in an embodiment.

Examples of steps for preparing a spray solution, which is used in the spray drying, include the steps of:
(1) dissolving and/or suspending polyvinyl alcohol having a saponification degree of 63 mol % or more and 67 mol % or less in water,
(2) adding methanol to (1) to prepare a mixed solution, and
(3) adding a poorly-soluble drug to the mixed solution of (2) to prepare a spray solution.

An apparatus for spray drying is not particularly limited, so long as a poorly-soluble drug can be formed into an amorphous form, or a solid dispersion of a poorly-soluble drug and polyvinyl alcohol having a saponification degree of 63 mol % or more and 67 mol % or less can be obtained. Examples of the apparatus include a spray dryer. The conditions for spray drying are not particularly limited, so long as the solid dispersion of a poorly-soluble drug and polyvinyl alcohol having a saponification degree of 63 mol % or more and 67 mol % or less can be obtained.

A method for drying is not particularly limited, so long as it is a conventional method in which it can be pharmaceutically dried. Examples of an apparatus include a forced-air dryer, a dryer under reduced pressure, a vacuum dryer, a fluidized bed dryer, and the like.

(II) Hot Melt Extrusion Method

In the hot melt extrusion method, a poorly-soluble drug and polyvinyl alcohol having a saponification degree of 63 mol % or more and 67 mol % or less are heated and melted, and then, cooled.

The temperature during heating and melting can be appropriately set in accordance with the melting point of the poorly-soluble drug, or the glass transition temperature of the polyvinyl alcohol.

An apparatus is not particularly limited, so long as a poorly-soluble drug can be formed into an amorphous form, or the solid dispersion of a poorly-soluble drug and polyvinyl alcohol having a saponification degree of 63 mol % or more and 67 mol % or less can be obtained. Examples thereof include a twin-screw extruder.

A method for pulverization is not particularly limited, so long as it is a conventional method in which it can be pharmaceutically pulverized. Examples of an apparatus include an impact mill (Hosokawa Micron Corporation; Fine Impact Mill), a dry & wet mill (Powrex Corporation: Comil), a cutting mill granulator (Dalton Corporation; Power Mill), and the like.

(III) Pulverization Method

In the pulverization method, a poorly-soluble drug and polyvinyl alcohol having a saponification degree of 63 mol % or more and 67 mol % or less are mixed and pulverized.

An apparatus is not particularly limited, so long as a poorly-soluble drug can be formed into an amorphous form, or a solid dispersion of a poorly-soluble drug and polyvinyl alcohol having a saponification degree of 63 mol % or more and 67 mol % or less can be obtained. Examples thereof include a planetary ball mill (for example, a ball mill manufactured by Ito Seisakusho Co., Ltd.), and the like.

The present invention includes a use of polyvinyl alcohol having a saponification degree of 63 mol % or more and 67 mol % or less in the manufacture of a pharmaceutical composition comprising a poorly-soluble drug and having an improved solubility.

With respect to the terms "a poorly-soluble drug" and "polyvinyl alcohol having a saponification degree of 63 mol % or more and 67 mol % or less", which are used in the use of the present invention, the explanations therefor described in the pharmaceutical composition of the present invention can be directly applied.

EXAMPLES

The present invention will now be further illustrated by, but is by no means limited to, the following Examples, Comparative Examples, and Experimental Examples.

Example 1

To 40 mL of water, 2 g of polyvinyl alcohol (POVAL, JMR-10M, JAPAN VAM & POVAL CO., LTD., saponification degree: 63.0 mol % to 67.0 mol %, hereinafter sometimes abbreviated as "A1") was added, and stirred until polyvinyl alcohol was dissolved. Further, 160 mL of methanol was added to prepare a mixed solution. To the mixed solution, 2 g of nifedipine (Wako Pure Chemical Industries, Ltd., Solubility in water: 10 μg/mL, unless otherwise stated, the same compound was used in the following) was added as a drug, and stirred until nifedipine was dissolved to prepare a spray solution. The spray solution was spray-dried with a spray dryer (Niro SD-Micro™ Spray Dryer, GEA, unless otherwise stated, the same apparatus was used in the following) to obtain a pharmaceutical composition (a solid dispersion) of Example 1.

Comparative Example 1

To 40 mL of water, 2 g of polyvinyl alcohol (GOHSENOL (registered trademark) OKS-5059, The Nippon Synthetic Chemical Industry Co., Ltd., saponification degree: 78.5 mol % to 82.0 mol %, hereinafter sometimes abbreviated as "B1") was added, and stirred until polyvinyl alcohol was dissolved. Further, 160 mL of methanol was added to prepare a mixed solution. To the mixed solution, 2 g of nifedipine was added as a drug, and stirred until nifedipine was dissolved to prepare a spray solution. The spray solution was spray-dried with a spray dryer to obtain a pharmaceutical composition (a solid dispersion) of Comparative Example 1.

Comparative Example 2

To 40 mL of water, 2 g of hypromellose 2910 (TC-5R, Shin-Etsu Chemical Co., Ltd., hereinafter sometimes abbreviated as "B2") was added, and stirred until B2 was dissolved. Further, 160 mL of methanol was added to prepare a mixed solution. To the mixed solution, 2 g of nifedipine was added as a drug, and stirred until nifedipine was dissolved to prepare a spray solution. The spray solution was spray-dried with a spray dryer to obtain a pharmaceutical composition (a solid dispersion) of Comparative Example 2.

<<Experimental Example 1>> Dissolution Test

A dissolution test of the pharmaceutical compositions (solid dispersions) prepared in Example 1, Comparative Example 1, and Comparative Example 2 (containing 30 mg equivalent of nifedipine) was carried out. The formulation of each pharmaceutical composition is shown in Table 1.

Mixed powder prepared by weighing the same weight of mannitol (PEARLITOL 200SD, Roquette, unless otherwise stated, the same compound was used in the following) as that of each pharmaceutical composition (solid dispersion) into a mortar, and mixing them using a pestle was used for the test. As the dissolution test, a Dissolution Test, a paddle method of the Japanese Pharmacopoeia was used. The dissolution test was carried out, using water (test fluid volume: 500 mL, fluid temperature: 37° C.) as a dissolution test fluid, at a paddle rotation speed of 50 rpm (250 rpm for 0 to 3 minutes from the beginning of the test, and 200 rpm for 3 to 5 minutes).

Sampling was carried out at regular intervals through a fine filter (F-72, Toyama Sangyo Co., Ltd., unless otherwise stated, the same filter was used in the following), and the ultraviolet absorbance of nifedipine was measured at 354 nm and 450 nm using an ultraviolet spectrophotometer (UV-1800, Shimadzu Corporation).

TABLE 1

|  | Ex. 1 | Comp. 1 | Comp. 2 |
| --- | --- | --- | --- |
| Nifedipine | 30 | 30 | 30 |
| A1 | 30 | — | — |
| B1 | — | 30 | — |
| B2 | — | — | 30 |

(Unit: mg)

The result of calculating the ratio of the dissolved concentration after 10 minutes from the beginning of the dissolution test with respect to the solubility (10 μg/mL) of the crystalline drug substance as an increasing ratio in dissolved concentration is shown in Table 2. A 6-fold or more increase in dissolved concentration was observed compared to the crystalline drug substance in the pharmaceutical composition (solid dispersion) of Example 1, whereas the increasing ratios in dissolved concentration were respectively approximately 2.6 and approximately 3.4 in the pharmaceutical compositions (solid dispersions) of Comparative Example 1 and Comparative Example 2.

TABLE 2

|  | Ex. 1 | Comp. 1 | Comp. 2 |
| --- | --- | --- | --- |
| Increasing ratio in dissolved concentration | 6.6 | 2.6 | 3.4 |

Example 2

A pharmaceutical composition (a solid dispersion) of Example 2 was obtained by mixing and pulverizing 750 mg of amenamevir (Astellas Pharma Inc., Solubility in water: 5 μg/mL, unless otherwise stated, the same compound was used in the following) as a drug and 2250 mg of "A1" powder using a planetary ball mill (LA-PO, Ito Seisakusho Co., Ltd.). The pharmaceutical composition (solid dispersion) of Example 2 was subjected to an X-ray diffraction measurement to confirm that no peak derived from the crystalline drug was detected.

Comparative Example 3

A pharmaceutical composition (a solid dispersion) of Comparative Example 3 was obtained by mixing and pulverizing 750 mg of amenamevir as a drug and 2250 mg of polyvinyl alcohol (GOHSENOL, NK-05R, The Nippon Synthetic Chemical Industry Co., Ltd., saponification degree: 71.0 mol % to 75.0 mol %, hereinafter sometimes abbreviated as "B3") using a planetary ball mill (LA-PO, Ito Seisakusho Co., Ltd.). The pharmaceutical composition (solid dispersion) of Comparative Example 3 was subjected to an X-ray diffraction measurement to confirm that no peak derived from the crystalline drug was detected.

Comparative Example 4

A pharmaceutical composition (a solid dispersion) of Comparative Example 4 was obtained by mixing and pulverizing 750 mg of amenamevir as a drug and 2250 mg of polyvinyl alcohol (GOHSENOL, KL-05, The Nippon Synthetic Chemical Industry Co., Ltd., saponification degree: 78.5 mol % to 82.0 mol %, hereinafter sometimes abbreviated as "B4") using a planetary ball mill (LA-PO, Ito Seisakusho Co., Ltd.). The pharmaceutical composition (solid dispersion) of Comparative Example 4 was subjected to an X-ray diffraction measurement to confirm that no peak derived from the crystalline drug was detected.

Comparative Example 5

A pharmaceutical composition (a solid dispersion) of Comparative Example 5 was obtained by mixing and pulverizing 750 mg of amenamevir as a drug and 2250 mg of polyvinyl alcohol (GOHSENOL, EG-05P, The Nippon Synthetic Chemical Industry Co., Ltd., saponification degree: 86.5 mol % to 89.0 mol %, hereinafter sometimes abbreviated as "B5") using a planetary ball mill (LA-PO, Ito Seisakusho Co., Ltd.). The pharmaceutical composition (solid dispersion) of Comparative Example 5 was subjected to an X-ray diffraction measurement to confirm that no peak derived from the crystalline drug was detected.

Comparative Example 6

A pharmaceutical composition (a solid dispersion) of Comparative Example 6 was obtained by mixing and pulverizing 750 mg of amenamevir as a drug and 2250 mg of polyvinyl alcohol (GOHSENOL, NL-05, The Nippon Synthetic Chemical Industry Co., Ltd., saponification degree: 98.5 mol % or more, hereinafter sometimes abbreviated as "B6") using a planetary ball mill (LA-PO, Ito Seisakusho Co., Ltd.). The pharmaceutical composition (solid dispersion) of Comparative Example 6 was subjected to an X-ray diffraction measurement to confirm that no peak derived from the crystalline drug was detected.

<<Experimental Example 2>> Dissolution Test

A dissolution test of the pharmaceutical compositions (solid dispersions) prepared in Example 2, Comparative Example 3, Comparative Example 4, Comparative Example 5, and Comparative Example 6 (containing 100 mg equivalent of amenamevir) was carried out. The formulation of each pharmaceutical composition is shown in Table 3.

Mixed powder prepared by weighing the same weight of mannitol as that of each pharmaceutical composition (solid dispersion) into a mortar, and mixing them using a pestle was used for the test. As the dissolution test, a Dissolution Test, a paddle method of the Japanese Pharmacopoeia was used. The dissolution test was carried out, using water (test fluid volume: 500 mL, fluid temperature: 37° C.) as a dissolution test fluid, at a paddle rotation speed of 50 rpm (250 rpm for 0 to 3 minutes from the beginning of the test, and 200 rpm for 3 to 5 minutes).

Sampling was carried out at regular intervals through a fine filter, and the ultraviolet absorbance of amenamevir was measured at 273 nm and 450 nm using an ultraviolet spectrophotometer (UV-1800, Shimadzu Corporation).

TABLE 3

|  | Ex. 2 | Comp. 3 | Comp. 4 | Comp. 5 | Comp. 6 |
| --- | --- | --- | --- | --- | --- |
| Amenamevir | 100 | 100 | 100 | 100 | 100 |
| A1 | 300 | — | — | — | — |
| B3 | — | 300 | — | — | — |
| B4 | — | — | 300 | — | — |
| B5 | — | — | — | 300 | — |
| B6 | — | — | — | — | 300 |

(Unit: mg)

The results of calculating the ratio of the dissolved concentration after 10 minutes from the beginning of the dissolution test with respect to the solubility (5 μg/mL) of the crystalline drug substance as an increasing ratio in dissolved concentration are shown in Table 4. An approximately 33.1-fold increase in dissolved concentration was observed compared to the crystalline drug substance in the pharmaceutical composition (solid dispersion) of Example 2, whereas the increasing ratios in dissolved concentration were approximately 8.7 to 33.1 in the pharmaceutical compositions (solid dispersions) of Comparative Example 3, Comparative Example 4, Comparative Example 5, and Comparative Example 6.

TABLE 4

|  | Ex. 2 | Comp. 3 | Comp. 4 | Comp. 5 | Comp. 6 |
| --- | --- | --- | --- | --- | --- |
| Increasing ratio in dissolved concentration | 33.1 | 28.4 | 28.0 | 22.0 | 8.7 |

Example 3

In 270 mL of water, 22.5 g of "A1" was stirred until dissolved. To a mixed solution prepared by further adding 1080 mL of methanol to the "A1" solution, 4.5 g of tacrolimus (Astellas Pharma Inc., Solubility in water: 4 μg/mL, unless otherwise stated, the same compound was used in the following) was added and stirred until dissolved to prepare a spray solution. The spray solution was spray-dried with a spray dryer to obtain a pharmaceutical composition (a solid dispersion) of Example 3.

<<Experimental Example 3>> Dissolution Test

A dissolution test of the pharmaceutical composition (solid dispersion) prepared in Example 3 (containing 20 mg equivalent of tacrolimus) was carried out. The formulation of the pharmaceutical composition is shown in Table 5.

Mixed powder prepared by weighing the same weight of mannitol as that of the pharmaceutical composition (solid dispersion) into a mortar, and mixing them using a pestle was used for the test. As the dissolution test, a Dissolution Test, a paddle method of the Japanese Pharmacopoeia was used. The dissolution test was carried out, using water (test fluid volume: 100 mL, fluid temperature: 37° C.) as a dissolution test fluid, at a paddle rotation speed of 50 rpm. Sampling was carried out using a Syringe 1 mL (Terumo Corporation) at regular intervals, and each sample was centrifuged at 12720×g for 5 minutes using a centrifuge. The drug concentration in each supernatant after centrifugation was analyzed by high performance liquid chromatography (HPLC, Waters), and the dissolution rate was calculated from the peak area. The HPLC analysis was carried out under the following conditions:

As a column, ChemcoPak NUCLEOSIL 5C8 (inner diameter: 4.6 mm, length: 15 cm, GL Sciences Inc.) was used, and the column temperature was 50° C.

As a mobile phase, acetonitrile (for HPLC, Kanto Chemical Co., Inc.)/methanol (for HPLC, Kanto Chemical Co., Inc.)/phosphoric acid (Kanto Chemical Co., Inc.)/water was used at a ratio of 460/180/1/360.

The measurement was carried out at a flow rate of 0.5 mL/min., and the injection volume was 100 μL.

TABLE 5

| | Ex. 3 |
|---|---|
| Tacrolimus | 20 |
| A1 | 100 |

(Unit: mg)

The result of an increasing ratio in dissolved concentration after 30 minutes from the beginning of the dissolution test, compared to the crystalline drug substance, is shown in Table 6. An approximately 29-fold increase in dissolved concentration was observed compared to the crystalline drug substance in the pharmaceutical composition (solid dispersion) of Example 3.

TABLE 6

| | Ex. 3 |
|---|---|
| Increasing ratio in dissolved concentration | 28.6 |

Comparative Example 7

Although 2 g of polyvinyl alcohol (GOHSENX (registered trademark) LL-810, The Nippon Synthetic Chemical Industry Co., Ltd., saponification degree: 45.0 mol % to 51.0 mol %, hereinafter sometimes abbreviated as "B7") was added to 40 mL of water, and stirred for 1 hour, polyvinyl alcohol was not dissolved. When 160 mL of methanol was further added and stirred for 1 hour, polyvinyl alcohol was not dissolved.

From the results, since polyvinyl alcohol having a saponification degree of 45.0 mol % to 51.0 mol % and a poorly-soluble drug cannot be homogeneously mixed, it is inferred that a poorly-soluble drug does not become amorphous, or the amorphous state cannot be maintained, and thus, the solubility cannot be improved.

Comparative Example 8

To 40 mL of water, 2 g of "B3" was added, and stirred until polyvinyl alcohol was dissolved. To a mixed solution prepared by further adding 160 mL of methanol to the "B3" solution, 2 g of nifedipine as a drug was added, and stirred until nifedipine was dissolved to prepare a spray solution. The spray solution was spray-dried with a spray dryer to obtain a pharmaceutical composition (a solid dispersion) of comparative Example 8.

Comparative Example 9

A pharmaceutical composition (a solid dispersion) of Comparative Example 9 was obtained by mixing and pulverizing 750 mg of amenamevir as a drug and 2250 mg of "B7" powder using a planetary ball mill (LA-PO, Ito Seisakusho Co., Ltd.).

Comparative Example 10

To 270 mL of water, 22.5 g of "B1" was added and stirred until dissolved. To a mixed solution prepared by further adding 1080 mL of methanol to the "B1" solution, 4.5 g of tacrolimus was added and stirred until dissolved to prepare a spray solution. The spray solution was spray-dried with a spray dryer to obtain a pharmaceutical composition (a solid dispersion) of comparative Example 10.

Comparative Example 11

To 270 mL of water, 22.5 g of "B2" was added and stirred until dissolved. To a mixed solution prepared by further adding 1080 mL of methanol to the "B2" solution, 4.5 g of tacrolimus was added and stirred until dissolved to prepare a spray solution. The spray solution was spray-dried with a spray dryer to obtain a pharmaceutical composition (a solid dispersion) of comparative Example 11.

Comparative Example 12

To 120 mL of water, 10.0 g of "B3" was added and stirred until dissolved. To a mixed solution prepared by further adding 480 mL of methanol to the "B3" solution, 2.0 g of tacrolimus was added and stirred until dissolved to prepare a spray solution. The spray solution was spray-dried with a spray dryer to obtain a pharmaceutical composition (a solid dispersion) of comparative Example 12.

<<Experimental Example 4>> Dissolution Test

A dissolution test of the pharmaceutical composition (solid dispersion) prepared in Comparative Example 8 (containing 30 mg equivalent of nifedipine) was carried out, as similar to Experimental Example 1. The formulation of the pharmaceutical composition is shown in Table 7.

TABLE 7

| | Comp. 8 |
|---|---|
| Nifedipine | 30 |
| B3 | 30 |

(Unit: mg)

The result of calculating the ratio of the dissolved concentration after 10 minutes from the beginning of the dissolution test with respect to the solubility of the crystalline drug substance as an increasing ratio in dissolved concentration is shown in Table 8. The increasing ratio in dissolved concentration of the pharmaceutical composition (solid dispersion) of Comparative Example 8 was approximately 3.8.

TABLE 8

| | Comp. 8 |
|---|---|
| Increasing ratio in dissolved concentration | 3.8 |

<<Experimental Example 5>> Crystalline Form Confirmation Test by X-Ray Diffraction Measurement A crystalline form confirmation test of the pharmaceutical compositions (solid dispersions) prepared in Example 1, Comparative Example 1, Comparative Example 2, and Comparative Example 8 was carried out. Measurement samples in which each pharmaceutical composition was uniformly fixed on a glass plate were prepared, and the measurement was carried out using a θ/θ rotating anode XRD diffractometer (Rigaku, RINT-TTRII).

Figure 1:
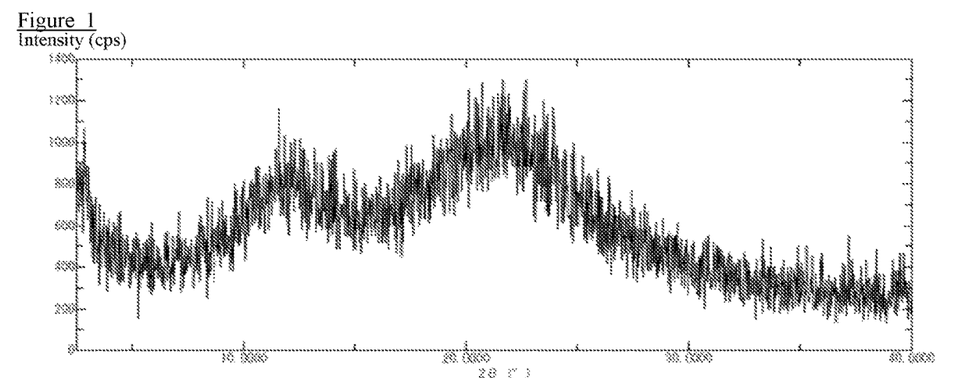
FIG. 1 is an X-ray diffraction profile obtained by X-ray diffraction measurement of a pharmaceutical composition prepared in Example 1.
Figure 2:
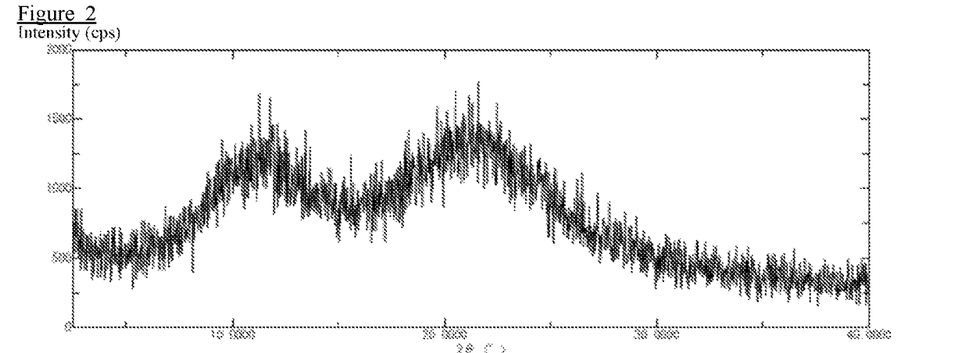
FIG. 2 is an X-ray diffraction profile obtained by X-ray diffraction measurement of a pharmaceutical composition prepared in Comparative Example 1.
Figure 3:
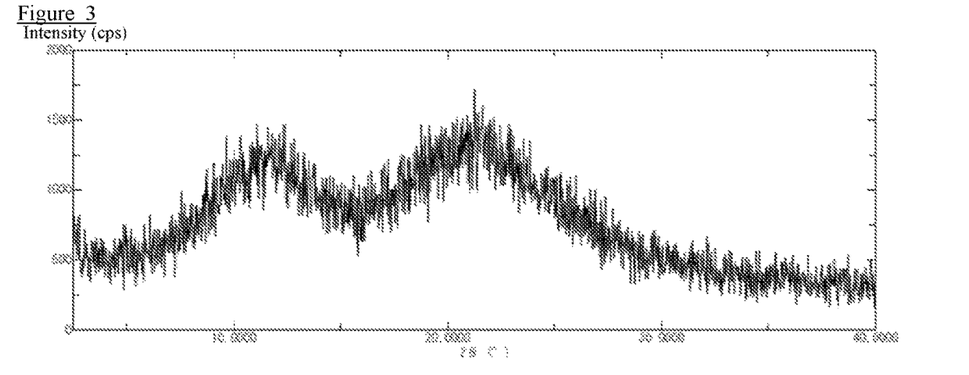
FIG. 3 is an X-ray diffraction profile obtained by X-ray diffraction measurement of a pharmaceutical composition prepared in Comparative Example 2.
Figure 4:
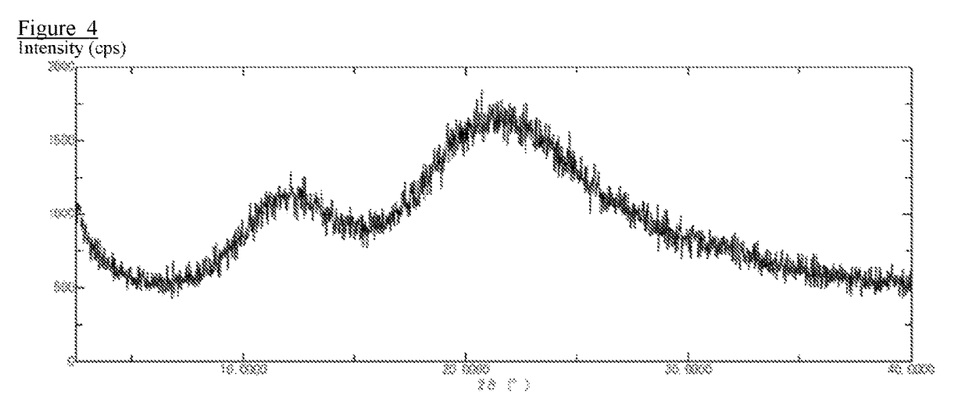
FIG. 4 is an X-ray diffraction profile obtained by X-ray diffraction measurement of a pharmaceutical composition prepared in Comparative Example 8.

The results of the crystalline form confirmation test are shown in FIG. 1 to FIG. 4. The pharmaceutical compositions (solid dispersions) of Example 1, Comparative Example 1, Comparative Example 2, and Comparative Example 8 were subjected to an X-ray diffraction measurement to confirm that no peak derived from the crystalline drug was detected.

<<Experimental Example 6>> Dissolution Test

A dissolution test of the pharmaceutical composition (solid dispersion) prepared in Comparative Example 9 (containing 100 mg equivalent of amenamevir) was carried out, as similar to Experimental Example 2. The formulation of the pharmaceutical composition is shown in Table 9.

TABLE 9

|  | Comp. 9 |
|---|---|
| Amenamevir | 100 |
| B7 | 300 |

(Unit: mg)

The result of calculating the ratio of the dissolved concentration after 10 minutes from the beginning of the dissolution test with respect to the solubility of the crystalline drug substance as an increasing ratio in dissolved concentration is shown in Table 10. The increasing ratio in dissolved concentration of the pharmaceutical composition (solid dispersion) of Comparative Example 9 was approximately 5.0.

TABLE 10

|  | Comp. 9 |
|---|---|
| Increasing ratio in dissolved concentration | 5.0 |

<<Experimental Example 7>> Crystalline Form Confirmation Test by X-Ray Diffraction Measurement A crystalline form confirmation test of the pharmaceutical compositions (solid dispersions) prepared in Example 2, Comparative Example 3, Comparative Example 4, Comparative Example 5, and Comparative Example 6 was carried out. Measurement samples in which each pharmaceutical composition was uniformly fixed on a glass plate were prepared, and the measurement was carried out using a θ/θ rotating anode XRD diffractometer (Rigaku, RINT-TTRII).

Figure 5:
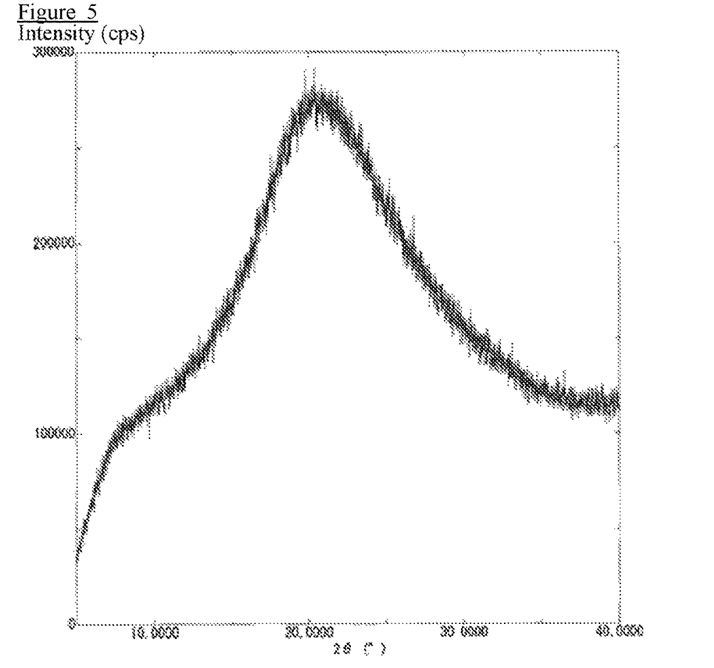
FIG. 5 is an X-ray diffraction profile obtained by X-ray diffraction measurement of a pharmaceutical composition prepared in Example 2.
Figure 6:
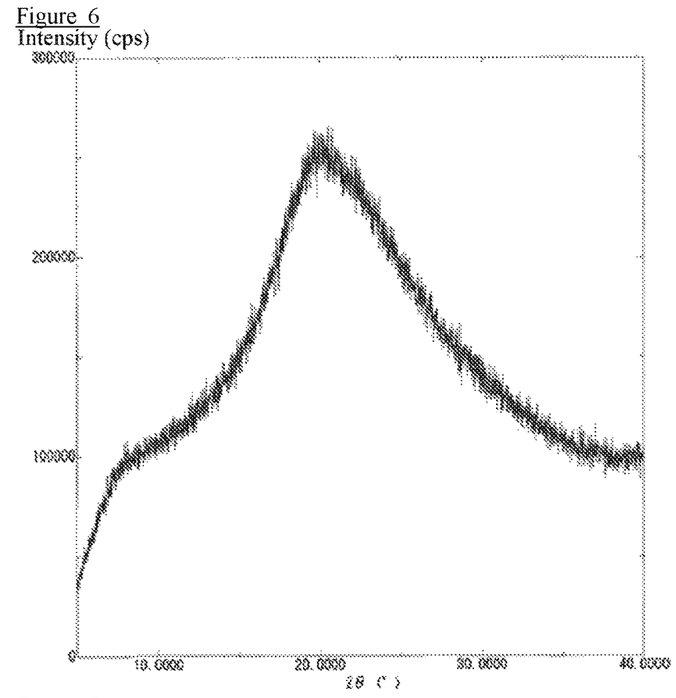
FIG. 6 is an X-ray diffraction profile obtained by X-ray diffraction measurement of a pharmaceutical composition prepared in Comparative Example 3.
Figure 7:
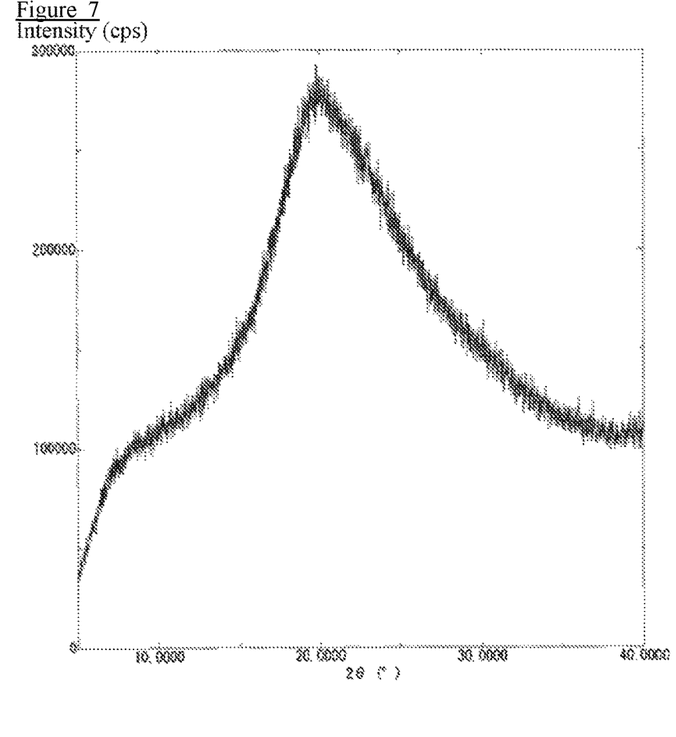
FIG. 7 is an X-ray diffraction profile obtained by X-ray diffraction measurement of a pharmaceutical composition prepared in Comparative Example 4.
Figure 8:
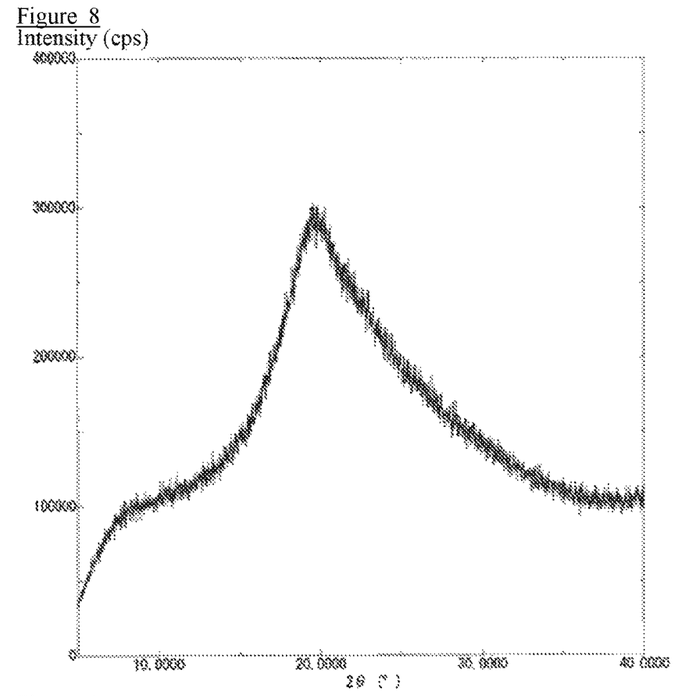
FIG. 8 is an X-ray diffraction profile obtained by X-ray diffraction measurement of a pharmaceutical composition prepared in Comparative Example 5.
Figure 9:
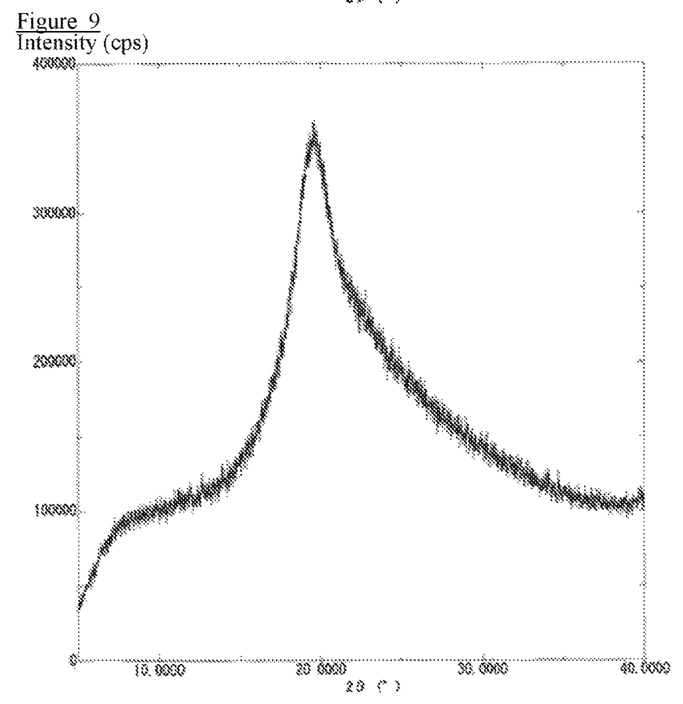
FIG. 9 is an X-ray diffraction profile obtained by X-ray diffraction measurement of a pharmaceutical composition prepared in Comparative Example 6.

The results of the crystalline form confirmation test are shown in FIG. 5 to FIG. 9. The pharmaceutical compositions (solid dispersions) of Example 2, Comparative Example 3, Comparative Example 4, Comparative Example 5, and Comparative Example 6 were subjected to an X-ray diffraction measurement to confirm that no peak derived from the crystalline drug was detected.

<<Experimental Example 8>> Dissolution Test

A dissolution test of the pharmaceutical compositions (solid dispersions) prepared in Comparative Example 10, Comparative Example 11, and Comparative Example 12 (containing 20 mg equivalent of tacrolimus) was carried out, as similar to Experimental Example 3. The formulation of each pharmaceutical composition is shown in Table 11.

TABLE 11

|  | Comp. 10 | Comp. 11 | Comp. 12 |
|---|---|---|---|
| Tacrolimus | 20 | 20 | 20 |
| B1 | 100 | — | — |
| B2 | — | 100 | — |
| B3 | — | — | 100 |

(Unit: mg)

The results of calculating the ratio of the dissolved concentration after 30 minutes from the beginning of the dissolution test with respect to the solubility of the crystalline drug substance as an increasing ratio in dissolved concentration are shown in Table 12. The increasing ratio in dissolved concentration of the pharmaceutical composition (solid dispersion) of Comparative Example 10 was approximately 19.4, and the increasing ratios in dissolved concentration of Comparative Example 11 and Comparative Example 12 were respectively approximately 18.9 and approximately 22.5.

TABLE 12

|  | Comp. 10 | Comp. 11 | Comp. 12 |
|---|---|---|---|
| Increasing ratio M dissolved concentration | 19.4 | 18.9 | 22.5 |

<<Experimental Example 9>> Crystalline Form Confirmation Test by X-Ray Diffraction Measurement A crystalline form confirmation test of the pharmaceutical compositions (solid dispersions) prepared in Example 3, Comparative Example 10, Comparative Example 11, and Comparative Example 12 was carried out. Measurement samples in which each pharmaceutical composition was uniformly fixed on a glass plate were prepared, and the measurement was carried out using a θ/θ rotating anode XRD diffractometer (Rigaku, RINT-TTRII).

Figure 10:
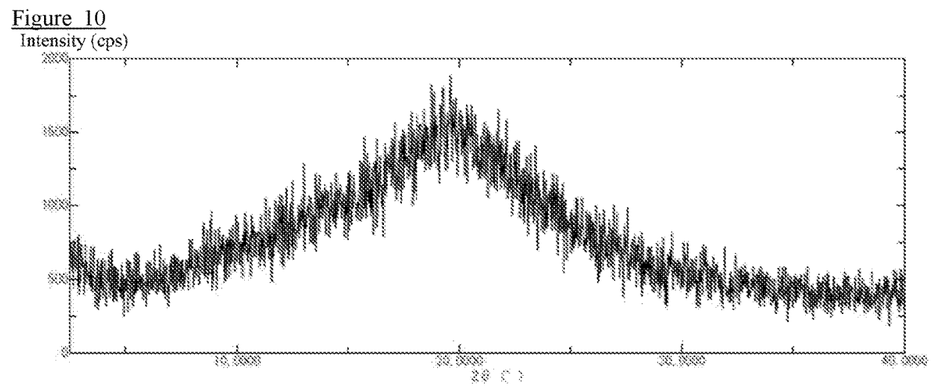
FIG. 10 is an X-ray diffraction profile obtained by X-ray diffraction measurement of a pharmaceutical composition prepared in Example 3.
Figure 11:
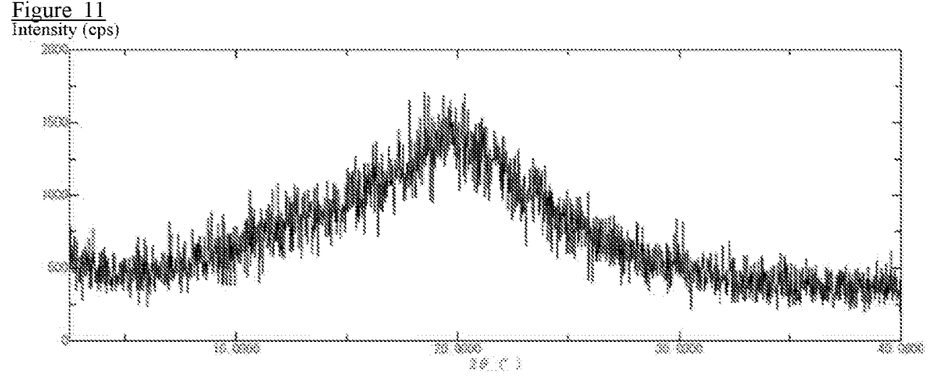
FIG. 11 is an X-ray diffraction profile obtained by X-ray diffraction measurement of a pharmaceutical composition prepared in Comparative Example 10.
Figure 12:
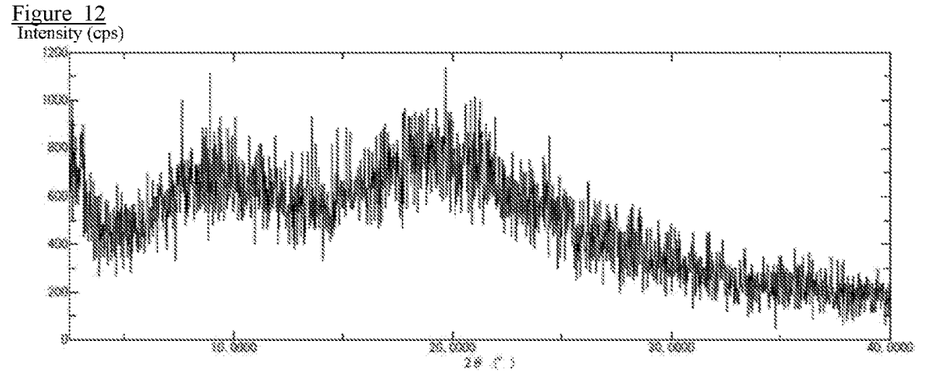
FIG. 12 is an X-ray diffraction profile obtained by X-ray diffraction measurement of a pharmaceutical composition prepared in Comparative Example 11.
Figure 13:
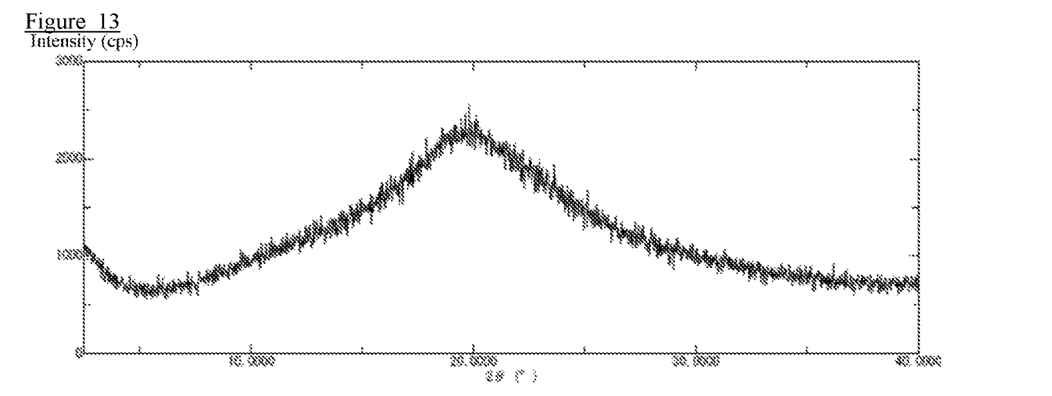
FIG. 13 is an X-ray diffraction profile obtained by X-ray diffraction measurement of a pharmaceutical composition prepared in Comparative Example 12.

The results of the crystalline form confirmation test are shown in FIG. 10 to FIG. 13. The pharmaceutical compositions (solid dispersions) of Example 3, Comparative Example 10, Comparative Example 11, and Comparative Example 12 were subjected to an X-ray diffraction measurement to confirm that no peak derived from the crystalline drug was detected.

INDUSTRIAL APPLICABILITY

According to the present invention, a pharmaceutical composition wherein the solubility of a poorly-soluble drug is improved can be provided.

Although the present invention has been described with reference to specific embodiments, various changes and modifications obvious to those skilled in the art are possible without departing from the scope of the appended claims.

The invention claimed is:

1. A solid pharmaceutical composition comprising a poorly-soluble drug, and polyvinyl alcohol having a saponification degree of 63 mol % or more and 67 mol % or less, wherein the poorly-soluble drug is amorphous.

2. The pharmaceutical composition according to claim 1, wherein the poorly-soluble drug has a solubility of 10 μg/mL or less in water.

3. The pharmaceutical composition according to claim 1, comprising a solid dispersion comprising the poorly-soluble drug and the polyvinyl alcohol.

\* \* \* \* \*